United States Patent
Bernard et al.

(10) Patent No.: US 6,296,834 B1
(45) Date of Patent: Oct. 2, 2001

(54) ORAL CARE COMPOSITION

(75) Inventors: Laurence Marie Bernard; Alison Katharine Green; Elizabeth Sarah Mountney, all of Bebington (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/552,071

(22) Filed: Apr. 19, 2000

(30) Foreign Application Priority Data

Apr. 19, 1999 (EP) .................................................. 99302993

(51) Int. Cl.⁷ .................................................... A61K 7/16
(52) U.S. Cl. .................................. 424/56; 424/49; 424/57
(58) Field of Search .......................................... 424/49–58

(56) References Cited

U.S. PATENT DOCUMENTS

| | | | |
|---|---|---|---|
| 3,692,894 | * 9/1972 | Amo et al. ............................... | 424/56 |
| 4,111,844 | * 9/1978 | Poloney et al. . | |
| 4,150,151 | * 4/1979 | Pader et al. ............................. | 424/56 |
| 4,264,580 | * 4/1981 | Barberio et al. ........................ | 424/57 |
| 4,301,143 | * 11/1981 | Barberio et al. ........................ | 424/57 |
| 4,419,342 | * 12/1983 | Hayes et al. ............................ | 424/54 |
| 4,466,954 | * 8/1984 | Ichikawa et al. ....................... | 424/56 |
| 4,545,979 | * 10/1985 | Ambike et al. .......................... | 424/1 |
| 4,550,018 | * 10/1985 | Ambike et al. ......................... | 424/52 |
| 4,950,479 | * 8/1990 | Hill et al. ................................ | 424/49 |
| 5,032,385 | * 7/1991 | Reed et al. ............................. | 424/49 |
| 5,032,387 | * 7/1991 | Hill et al. ............................... | 424/49 |
| 5,188,820 | * 2/1993 | Cummins et al. . | |
| 5,240,696 | * 8/1993 | Van Der Ouderaa et al. . | |
| 5,328,682 | * 7/1994 | Pullen et al. ............................ | 424/49 |
| 5,348,733 | 9/1994 | Morishima et al. . | |
| 5,415,810 | * 5/1995 | Lee et al. ............................... | 252/545 |
| 5,500,217 | * 3/1996 | Austin et al. .......................... | 424/401 |
| 5,500,448 | * 3/1996 | Cummins et al. . | |
| 5,688,492 | * 11/1997 | Galley et al. .......................... | 424/49 |
| 5,747,004 | * 5/1998 | Giani et al. . | |
| 5,976,506 | * 11/1999 | Vernon et al. . | |
| 6,090,772 | * 7/2000 | Kaiser et al. ......................... | 510/388 |
| 6,107,261 | * 8/2000 | Taylor et al. ......................... | 510/131 |
| 6,204,230 | * 3/2001 | Taylor et al. ......................... | 510/131 |
| 6,218,345 | * 4/2001 | Brooks et al. ........................ | 510/123 |

FOREIGN PATENT DOCUMENTS 1 288 819 9/1972 (GB) .
2 112 284 12/1981 (GB) .

OTHER PUBLICATIONS

Henkel DE 1983 4355 A1 Dental Care Composition * 1.5% SDS * 0.13% Calcium Glycero Phosphate 0.190 Triclosan (filed Jul. 30, 1998).*
Henkel WO/PCT 2000 0006109 A1.*
EP/WO 5210 Jul. 21, 1999.*

* cited by examiner

Primary Examiner—Shep K. Rose
(74) Attorney, Agent, or Firm—Milton L. Honig

(57) ABSTRACT

The invention provides for an oral care composition which contains a non-cationic, water-insoluble or sparingly water-soluble antimicrobial agent, and an alkalimetal, ammonium or substituted ammonium alkylsulphate which contains a straight-chain, saturated or unsaturated C10 alkyl group. Such oral care composition provides for a higher antimicrobial efficacy than similar compositions which, however, contain predominantly an alkalimetal C12 alkylsulphate

6 Claims, No Drawings

ORAL CARE COMPOSITION

BACKGROUND OF THE INVENTION

The present invention relates to an oral care composition which comprises a non-cationic, water-insoluble or sparingly water-soluble antimicrobial agent.

1. FIELD OF THE INVENTION

2. The Related Art

Oral care compositions which comprise such an antimicrobial agent are well-known and have found their way to the market place. One of the most commonly used representatives of such antimicrobial agents is a halogenated diphenyl ether, 2',4,4'-trichloro-2-hydroxy-diphenyl ether, known under the trade name Triclosan. Other such antimicrobial agents are 2,2'-dihydroxy-5,5'-dibromo-diphenyl ether, 2,2'-methylenebis-(4-chloro-6- bromo-phenol), halogenated salicylanilides and halogenated cabanilides.

Such antimicrobial agents are usually included in the oral care compositions in an amount of 0.1 to 1.0 % by weight of the composition.

Oral care compositions nearly always contain an anionic synthetic detergent active material to produce the required foaming activity of the oral care composition upon use thereof by the consumer, and the most commonly used synthetic anionic detergent active materials are C8–C18 alkylsulphates, particularly sodium lauryl sulphate. Sodium lauryl sulphate (SLS) consists predominantly of sodium dodecyl sulphate, with lower amounts of sodium salts of sulphated higher alcohols, and minor amounts of sodium salts of lower sulphated alcohols and unsulphated alcohols.

SLS is usually included in the oral care compositions in an amount of 0.5–3.0% by weight of the composition, and typically in an amount of 1.5–2.7% by weight of the composition.

Other anionic synthetic detergent active materials are occasionally also used, such as sodium dodecylbenzenesulphonate (DOBS), either alone or, more commonly together with SLS. The amount of DOBS, or of a mixture of SLS and DOBS, used in an oral care composition is generally the same as indicated above for SLS.

SUMMARY OF THE INVENTION

We have now surprisingly found, that if the SLS in the above compositions is at least partly replaced by an alkalimetal, ammonium or substituted ammonium alkylsulphate, the alkyl group of which is predominantly a straight-chain, saturated or unsaturated C10 alkyl group (hereinafter briefly referred to as SDS), an unexpected enhancement of the efficacy of the antimicrobial agent can be obtained. This allows the formulator of an oral care composition not only to provide an oral care composition with an antimicrobial activity which is significantly higher than a composition with the same level of the antimicrobial agent and SLS, but also to use less of the antimicrobial agent and still obtain the same antimicrobial activity as that of a composition with the same level of SLS and the normal, higher level of the antimicrobial agent.

While the SDS can completely replace the SLS according to the present invention, the benefits of the invention are also already obtained when the SDS replaces at least 30% of the SLS. We have additionally found, that such partial replacement of SLS by SDS also provides for an increased foaming power, compared with certain sources of SLS, and a replacement of 50% of the SLS by the SDS provides for a foaming power which is equal or superior to the foaming power of the most commonly used type of SLS, at the same total level of active detergent.

DETAILED DESCRIPTION OF THE INVENTION

Consequently, in its broadest aspects, the present invention relates to an oral care composition which comprises a non-cationic, water-insoluble or sparingly water-soluble antimicrobial agent, and an alkalimetal, ammonium or substituted ammonium C8–C18 alkylsulphate and is characterised in that the alkalimetal, ammonium or substituted ammonium C8–C18 alkylsulphate comprises at least 30% by weight of an alkalimetal, ammonium or substituted ammonium alkylsulphate with a straight-chain, saturated or unsaturated C10 alkyl group.

In a preferred embodiment of the invention, the alkalimetal, ammonium or substituted ammonium C8–C18 alkylsulphate comprises at least 45% by weight of the alkalimetal, ammonium or substituted ammonium alkylsulphate with a straight-chain saturated C10 alkyl group, the balance being an alkalimetal, ammonium or substituted ammonium alkylsulphate with a straight-chain, saturated predominantly C12 or greater alkyl group.

In general, as said above, the total amount of alkylsulphates according to the present invention in the oral care composition ranges from 0.5–3.0% by weight of the composition, preferably 1.5–2.7% by weight of the composition. In case other synthetic anionic detergents such as DOBS are also to be included, the total amount of the alkylsulphates and such other anionic synthetic detergents should also lie within the above ranges, but such other anionic synthetic detergents may not be present in an amount, greater than 25% by weight of the amount of the alkylsulphates.

The preferred antimicrobial agent in the present invention is Triclosan, and the amount of the antimicrobial agent in the present invention ranges from 0.1–1.0% by weight of the composition, preferably from 0.1–0.3% by weight of the composition.

The oral care products of the present can be of any well-known type, such as pastes, liquids and gels.

The oral care compositions may comprise optional, conventional ingredients such as pharmaceutically acceptable carriers like starch, sucrose, water or water/alcohol systems etc. Small amounts of other surfactants may also be included, such as nonionic, cationic and zwitterionic or amphoteric surfactants. Preferred surfactants are nonionic surfactants such as ethylene oxide/propylene oxide block copolymers, e.g. Pluronic F 127, used in small amounts, e.g. about 0.25% by weight. They may comprise particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight. Water-soluble mildly abrasive salts like sodium bicarbonate and sodium carbonate may additionally be included. Preferred particulate abrasive materials are silicas and calcium carbonates, the latter including finely ground natural chalk as well as synthetically precipitated calcium carbonates.

Furthermore, they may comprise humectants such as glycerol, sorbitol, propyleneglycol, xylitol, lactitol and so on.

Binders and thickeners such as sodium carboxymethylcellulose, xanthan gum, gum arabic, carragheenan etc. may also be included, as well as synthetic polymers such as polyacrylates and carboxyvinyl polymers such as Carbopol®.

Flavours such as peppermint and spearmint oils may also be included, as well as preservatives such as sodium benzoate, opacifying agents, colouring agents, pH-adjusting agents, buffering agents such as potassium citrate and potassium tartrate, sweetening agents and so on.

Other anti-bacterial agents may also be included such as copper-, copper sulphate, copper-hinokitiol, copper-(ethyl) maltol, zinc- and stannous salts such as zinc citrate, sodium zinc citrate, stannous pyrophosphate and sanguinarine extract Polymeric compounds which can enhance the delivery of active ingredients such as anti-bacterial agents and anti caries agents such as fluorides can also be included. Examples of such polymers are copolymers of polyvinylmethylether with maleic anhydride and other similar delivery enhancing polymers, e.g. those described in DE-A-3,942,643 (Colgate)

Furthermore anti-inflammatory agents such as ibuprofen, flurbiprofen, aspirin, indomethacin etc. may also be included.

Anti-caries agents such as sodium- and stannous fluoride, aminefluorides, sodium monofluorophosphate, casein; plaque buffers such as urea, calcium lactate, calcium glycerophosphate, strontium polyacrylates may also be included. In this respect we have observed that the use of a low level (e.g. 0.5%) calcium glycerophosphate in the compositions of the invention further enhances the antimicrobial efficacy of the compositions. Other optional ingredients include vitamins such as Vitamin C, and plant extracts. Desensitising agents such as glycerol monooleate, potassium citrate, potassium chloride, potassium tartrate, potassium bicarbonate, potassium oxalate, potassium nitrate as well as strontium salts may also be included.

Buffers and salts to buffer the pH and ionic strength of the compositions may also be included Furthermore, the oral compositions may comprise anti-calculus agents such as alkalimetal pyrophosphates, hypophosphite-containing polymers, organic phosphonates, phosphocitrates etc.

In addition, the compositions may comprise functional biomolecules such as bacteriocins, antibodies, enzymes and so on.

Other optional ingredients that may be included are e.g. bleaching agents such as peroxy compounds e.g. organic peracids, potassium peroxydiphosphate; effervescing systems such as sodium bicarbonate/citric acid systems, colour change systems, and so on. The compositions may, furthermore, comprise (coloured) microcapsules which contain a solid or liquid core, to impart a speckled appearance to the compositions, particularly when the latter are in gel form.

The toothpastes may also be formulated into systems for use in dual-compartment type dispensers, or into striped toothpastes with various colours.

The present invention is further illustrated by way of Example.

EXAMPLE 1

The following toothpastes were prepared:

|  | 1 | 2 | 3 | 4 | 5 | 6 | 7 | 8 | 9 | 10 |
|---|---|---|---|---|---|---|---|---|---|---|
| Particulate chalk abrasive material | 35.0 | 35.0 | 35.0 | 35.0 | 35.0 | 35.0 | 35.0 | 35.0 | 35.0 | 35.0 |
| Sodium alkyl sulphate A* (100% active) | 2.5 | 2.5 | 2.5 | 1.75 | 0 | 0 | 0 | 0 | 1.25 | 0 |
| Sodium alkyl sulphate B** (39% active) | 0 | 0 | 0 | 0 | 6.41 | 6.41 | 6.41 | 4.48 | 3.2 | 6.41 |
| Triclosan | 0 | 0.30 | 0.30 | 0.30 | 0 | 0.30 | 0.30 | 0.30 | 0.30 | 0.20 |
| Calcium glycerophospate | 0 | 0 | 0.5 | 0 | 0 | 0 | 0.5 | 0 | 0 | 0 |
| Sodium carboxymethyl cellulose | 0.90 | 0.90 | 0.90 | 0.90 | 0.90 | 0.90 | 0.90 | 0.90 | 0.90 | 0.90 |
| Trisodium orthophosphate | 1.0 | 1.0 | 1.0 | 1.0 | 1.0 | 1.0 | 1.0 | 1.0 | 1.0 | 1.0 |
| Flavour | 1.15 | 1.15 | 1.15 | 1.15 | 1.15 | 1.15 | 1.15 | 1.15 | 1.15 | 1.15 |
| Water/sorbitol mixture (weight ratio 26:30) | 59.45 | 59.15 | 58.65 | 59.9 | 55.24 | 55.24 | 54.74 | 57.17 | 57.2 | 55.34 |

*the alkyl chain distribution was: $C_{10}$ 5% max., $C_{12}$ 45–100%, $C_{14}$ 45% max., $C_{16} + C_{18}$ 25% max.
**the alkyl chain distribution was: $C_8$ less than 10%, $C_{10}$ min. 90%, $C_{12}$ less than 4% (39% solution)

The toothpaste nos. 10 and 11 were tested in a salivary sediment model test similar to that described by R. L. Wijeijweera and I. Kleinberg in Archs. Oral Biol., Vol. 34, No. 1, 1989, pages 43–53, using ex vivo samples and measuring the amount of Triclosan delivered to the salivary sediment.

| Toothpaste Number | TCN (ppm) Delivered to Sediment* |
|---|---|
| 2 | 211.6 |
| 3 | 269.6 |
| 4 | 293.7 |
| 6 | 367.1 |
| 7 | 395.9 |
| 8 | 368.8 |
| 9 | 378.5 |
| 10 | 271.2 |

*ppm TCN per ml sediment suspension with A600 (OD) = 2.0. (A600 = absorbance at a wavelength of 600 nm; OD = optical density)

With toothpaste no. 2, 211.6 ppm Triclosan was measured in the salivary sediment, and with toothpaste no. 6, 367.1 ppm Triclosan was measured in the salivary sediment. This shows, that at the same level of Triclosan and SLS, with SDS a significantly increased efficacy of the Triclosan was obtained.

Comparing the results, obtained with toothpastes nos. 4 and 8 also shows a significantly improved efficacy of the Triclosan at a lower level of SDS (1.75%). A comparison of the results, obtained with toothpastes nos. 2 and 9 shows, that a partial replacement of SLS by SDS (50:50) also resulted in a significantly improved efficacy of the Triclosan. The results, obtained with toothpaste 10, compared with those, obtained with toothpaste 2, also showed a significantly improved efficacy of the Triclosan in the presence of SDS, while the level of Triclosan in toothpaste no. 10 was even lower than the level thereof in toothpaste no. 2. A comparison between the results of toothpastes nos. 3 and 7 showed, that the presence of the calcium glycerophosphate further significantly enhanced the efficacy of the Triclosan in the compositions of the present invention.

EXAMPLE 2

An in vitro biofilm regrowth assay test was carried out with the toothpastes nos. 1, 2, 4–6 and 8–10.

The test is based on monitoring the growth (by measuring absorbance) of a biofilm of a single oral isolate, formed in the wells of a 96 well plate, after treatment with toothpaste slurries, and calculating the time taken to reach a chosen turbidity (i.e. a chosen absorbance value at a wavelength of 630 nm)

A sample of *S. warneri* was cultured overnight in BHI medium. The culture was centrifuged and washed twice with phosphate-buffered saline (PBS) to an approximate optical density (OD) of 1.0.

Toothpaste slurries were prepared by mixing paste with saliva to give 33% (w/w) slurries. Wells were treated with toothpaste supernatant for 30 seconds. After treatment and washing, plates were incubated at 37° C. in a microtitre plate reader (Dynex Technologies DIAS) and growth monitored at 630 nm. The end-point was taken as the time taken to reach an A630 (OD) of 0.5.

The results are shown in the following table:

| Toothpaste Number | Time to OD 0.5 (in hours) |
| --- | --- |
| 1 | 5.17 |
| 2 | 8.81 |
| 4 | 10.50 |
| 5 | 6.56 |
| 6 | 12.80 |
| 8 | 12.00 |
| 9 | 11.99 |
| 10 | 11.57 |

The toothpastes according to the present invention, nos. 6, 8 and 9 are shown to be much more effective than the toothpastes, containing only SLS (nos. 2 and 4). Toothpaste no. 10 according to the present invention with 0.2% Triclosan was significantly better than toothpaste no. 2 which has 0.3% Triclosan and SLS instead of SDS.

EXAMPLE 3

In vitro foam tests with 1:3 saliva/toothpaste slurries of toothpastes nos. 6–10 showed equal or higher foam height than toothpaste nos. 2–4 containing Triclosan and SLS instead of SDS.

| Toothpaste Number | Foam Height (cm) |
| --- | --- |
| 1 | 2.3 |
| 2 | 2.4 |
| 3 | 1.8 |
| 4 | 1.9 |
| 5 | 3.3 |
| 6 | 3.2 |
| 7 | 3.6 |
| 8 | 2.6 |
| 9 | 2.5 |
| 10 | 3.3 |

What is claimed is:

1. An oral care composition comprising from about 0.1 to about 1% by weight of a non-cationic, water-insoluble or sparingly water-soluble antimicrobial agent, and a foaming effective amount of an alkali, ammonium or substituted ammonium C8–C18 alkylsulphate salt, wherein the C8–C18 alkylsulphate salt comprises at least 30% by weight of a straight-chain, saturated or unsaturated C10 alkyl group.

2. A composition according to claim 1, wherein the C8–C18 alkylsulphate salt comprises at least 45% by weight of the straight-chain, saturated C10 alkyl group, the balance being a straight-chain, saturated predominantly C12 alkyl or higher group.

3. A composition according to claim 1 characterised in that the antimicrobial agent is Triclosan.

4. A composition according to claim 1 characterised in that it further comprises calcium glycerophosphate.

5. An oral care composition comprising:

(i) from about 0.1 to about 1% by weight of a non-cationic, water-insoluble or sparingly water-soluble antimicrobial agent;

(ii) from about 0.5 to about 3% by weight of an alkalimetal, ammonium or substituted ammonium C8–C18 alkylsulphate detergent, wherein at least 30% by weight of the detergent is an alkalimetal, ammonium or substituted ammonium alkylsulphate with a straight-chain, saturated or unsaturated C10 alkyl group; and (iii) a sodium or stannous fluoride present in an effective amount to prevent caries.

6. A method for controlling microbial growth on a surface, comprising applying to the surface a composition comprising from about 0.1 to about 1% by weight of a non-cationic, water-insoluble or sparingly water-soluble antimicrobial agent, and a foaming effective amount of an alkali, ammonium or substituted ammonium C8–C18 alkylsulphate salt, wherein the C8–C18 alkylsulphate salt comprises at least 30% by weight of a straight-chain, saturated or unsaturated C10 alkyl group.

* * * * *